Figure 1:
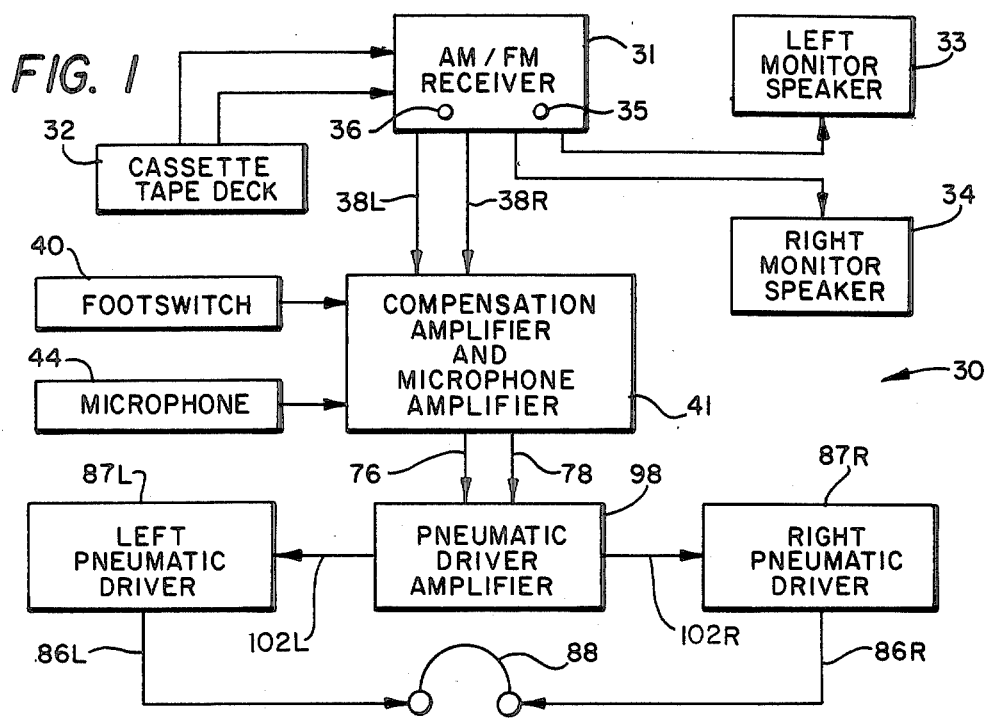

United States Patent [19]

Taylor

[11] Patent Number: 4,701,952
[45] Date of Patent: Oct. 20, 1987

[54] FREQUENCY ATTENUATION COMPENSATED PNEUMATIC HEADPHONE AND LIQUID TUBE AUDIO SYSTEM FOR MEDICAL USE

[76] Inventor: Jefferson H. Taylor, 9430 Covemeadow Dr., Dallas, Tex. 75238

[21] Appl. No.: 923,668

[22] Filed: Oct. 27, 1986

Related U.S. Application Data

[63] Continuation-in-part of Ser. No. 659,413, Oct. 10, 1984, abandoned.

[51] Int. Cl.$^4$ .............................................. H04R 5/00
[52] U.S. Cl. ........................................ 381/25; 381/67
[58] Field of Search .................... 181/20, 22; 367/132; 381/25, 67, 68.2, 98, 103

[56] References Cited

U.S. PATENT DOCUMENTS

| | | | |
|---|---|---|---|
| Re. 25,652 | 10/1964 | Kennedy | 381/25 |
| 3,920,904 | 11/1975 | Blauert et al. | 381/25 |
| 4,347,405 | 8/1982 | Davis | 381/25 |
| 4,352,200 | 9/1982 | Oxman | 381/86 |
| 4,528,690 | 7/1985 | Sedgwick | 381/67 |
| 4,565,258 | 1/1986 | Butler et al. | 381/25 |

Primary Examiner—Forester W. Isen
Attorney, Agent, or Firm—Warren H. Kintzinger

[57] ABSTRACT

A confined system of sound transmission from a frequency attenuation compensated source through plastic pneumatic tubes in series with liquid tubes of considerable length, transmitting audio to and through pneumatic headphones to the ear canals of the user. It is an audio system suitable for use in Nuclear Magnetic Resonance scanning environments and for use in CAT scan environments. The system includes a stereo program source playing into a stereo frequency compensation amplifier driving right and left loudspeaker pneumatic drivers feeding audio to and through long liquid tubes in series with pneumatic tubes extended to left and right earphones of plastic headphones worn by a patient in a scan room environment. The tubes that extend from the electronic audio system equipment outside the scan room through scan room walls to the patient headphones and the headphones themselves are made of plastic or other non-magnetic materials causing no interference with the scanning signals and are not visible on scan pictures produced.

19 Claims, 10 Drawing Figures

FREQUENCY ATTENUATION COMPENSATED PNEUMATIC HEADPHONE AND LIQUID TUBE AUDIO SYSTEM FOR MEDICAL USE

This is a continuation-in-part of my co-pending application, Ser. No. 659,413, filed Oct. 10, 1984 now abandoned.

This invention relates in general to audio amplification systems, and more particularly, to a frequency attenuation compensated pneumatic headphone and tube audio system with extended acoustic pneumatic and liquid tubes adapted for use from outside to inside a medical RF shielded room environment.

A medical environment where radio frequency (RF) shielding is important and where communication can be helpful to the patient is, for example, a typical Nuclear Magnetic Resonance (NMR) Imaging system consisting of a large cylindrical magnet with a center bore large enough to accomodate the body of a patient to be scanned. Associated with the magnet are electrical and electronic components which are a part of the scan system. The magnet and some of the associated parts are housed in a radio frequency (RF) shielded room which may also contain magnetic shielding materials. When the scan-room (shielded room) door is closed, communications through walls, doors or windows is usually quite difficult, particularly when the scanner is operating. The door must be closed when a scan is being performed, to prevent RF interference from entering the room and degrading or destroying the scan signals. Unless a patient is very ill, he is usually left in the scan room alone while a scan is being performed. Because the scanner generates a high noise level when operated, the patient has generally been provided with ear plugs to attenuate this noise, strapped to the patient bed, fitted with a scan coil (often on the head), positioned inside the magnetic bore, and told to remain perfectly still for the duration of the scan (usually 30 minutes or more). Often, the patient can see nothing outside the magnet, and feels totally cut-off from the rest of the world with the claustrophobic effect alone unnerving to some patients, and with time passing slowly for most of them. Added to these effects is the fact that the patient can hear nothing except the operation of the machine. It is important that a method be provided for the operator of the NMR Imaging system who is positioned outside of the scan room to communicate with the patient inside the scan room, and that in intervals between communications from the operator the patient be provided music or other program material of his choice. With the intense magnetic field located in the scan room, conventional loudspeakers are unsuitable for use, since their performance would be greatly degraded by the scan magnetic field. Conversely, the magnetic fields generated by the loudspeakers could be detrimental to the scan signals. In addition, electrical signals, used to drive the loudspeakers, could adversely affect the signals generated by the scanner, and penetrations from outside the room to the inside would require the use of RF filters. Since the presence of any metallic object within the scanned field adversely affects the scan picture itself, it would seem unlikely that even a non-magnetic audio transducer (loudspeaker) could be placed close enough to the patient to be heard above the noise of the scanner. Conceiveably, crystal headphones could be used, except the wires connecting them to the electrical current would cause unacceptable interference in the scan area even if they could otherwise be constructed of non-metallic parts.

It is therefore a principal object of this invention to provide a frequency attentuation compensated pneumatic headphone and liquid tube audio system for medical use with communication from an operator stationed outside a room to a patient within an RF shielded room.

Another object is to provide such an audio system without any electrical conductor penetration into a patient scan room.

A further object is to provide such an audio system that does not generate any extraneous magnetic fields in the patient scan room.

Still another object is to mask scan machine noise along with the ability to communicate both speech and music to a patient in a scan room.

Another object is to avoid introduction of metallic parts in the patient scan area and for the headset and acoustic tubes both pneumatic and liquid of the audio system within the treatment room to be transparent to NMR scanning.

A further object is to optimize patient comfort and safety.

Still another objects is for all components other than pneumatic and liquid tubes and headphones that require occasional maintainance to be outside of the scan room.

Features of the invention useful in accomplishing the above objects include, in a frequency attenuation compensated pneumatic headphone and liquid tube audio system for medical scan use, conventional electromagnetic loudspeakers housed in special enclosures (pneumatic drivers) located outside of the scan room. In those installations where magnetic shielding is not employed, the pneumatic drivers are located some distance from the scan room to reduce the effects of the high magnetic field generated by the magnet in the scan room. Typically, the pneumatic drivers are located as close as practical to the scan room, so that serially connected liquid and pneumatic tubes may be as short as practical, thereby insuring fidelity. Attached to the pneumatic drivers are plastic closed liquid acoustic tubes, that penetrate the scan room through guides which are usually pre-existing in these facilities, and connected serially through pneumatic tubes to pneumatic headphones worn by the patient. The materials (plastic) used in this headset cause no interference with the scanning signals and are not visible on the scan pictures produced. The pneumatic drivers are powered from a conventional audio amplifier driven with the program material. A frequency-response-shaping network is employed to attenuate the lower frequency audio spectrum, and to "boost" the higher frequencies (to compensate for the attenuation of high frequencies as the audio passes through the serially connected liquid and pneumatic tubes). A microphone is included for use by the operator so he may interrupt the program material and talk directly to the patient.

A specific embodiment representing what is presently regarded as the best mode of carrying out the invention is illustrated in the accompanying drawings.

Figure 4:
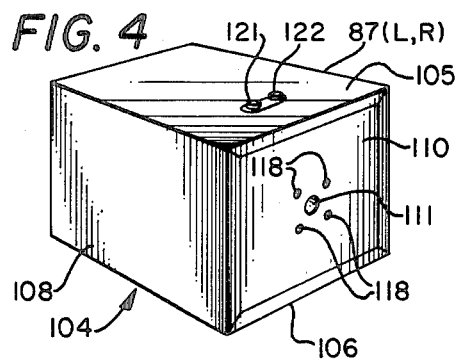
Figure 6:
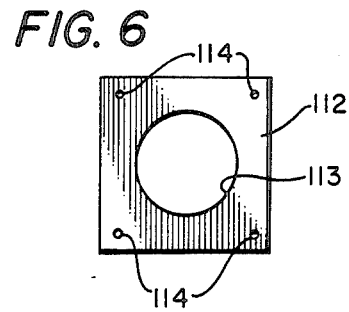
Figure 5:
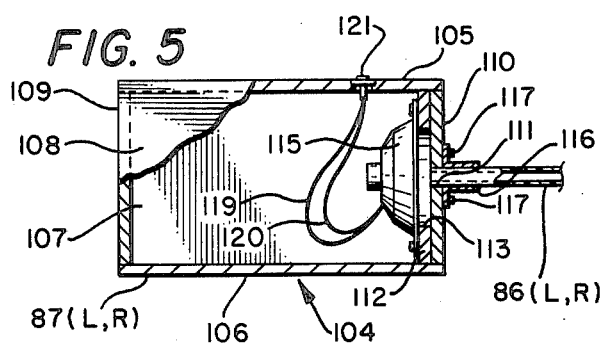
Figure 7:
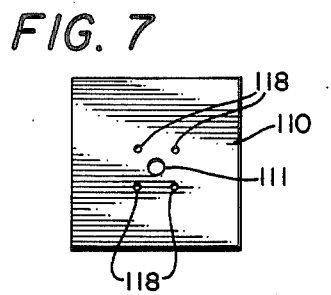
Figure 2:
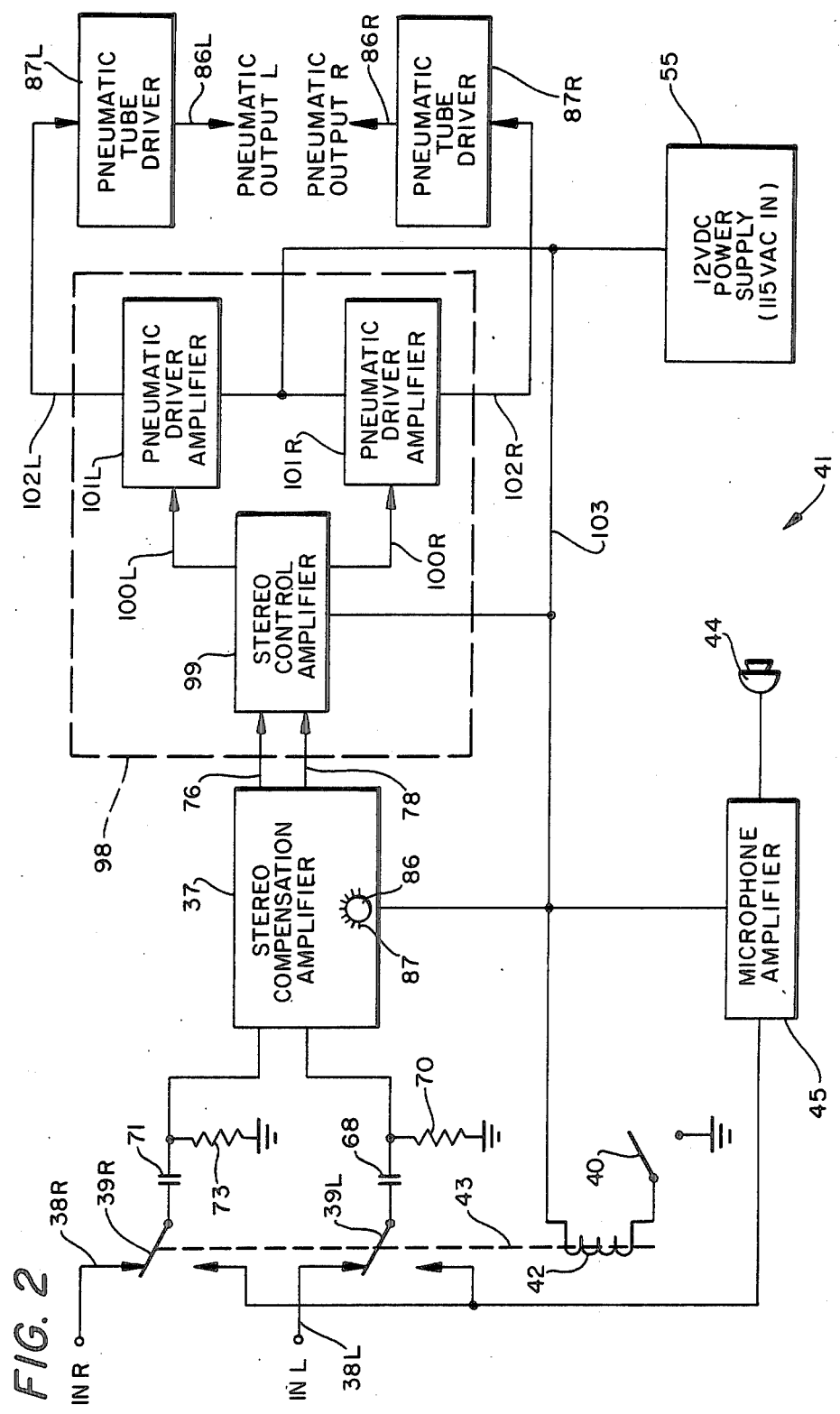
Figure 3:
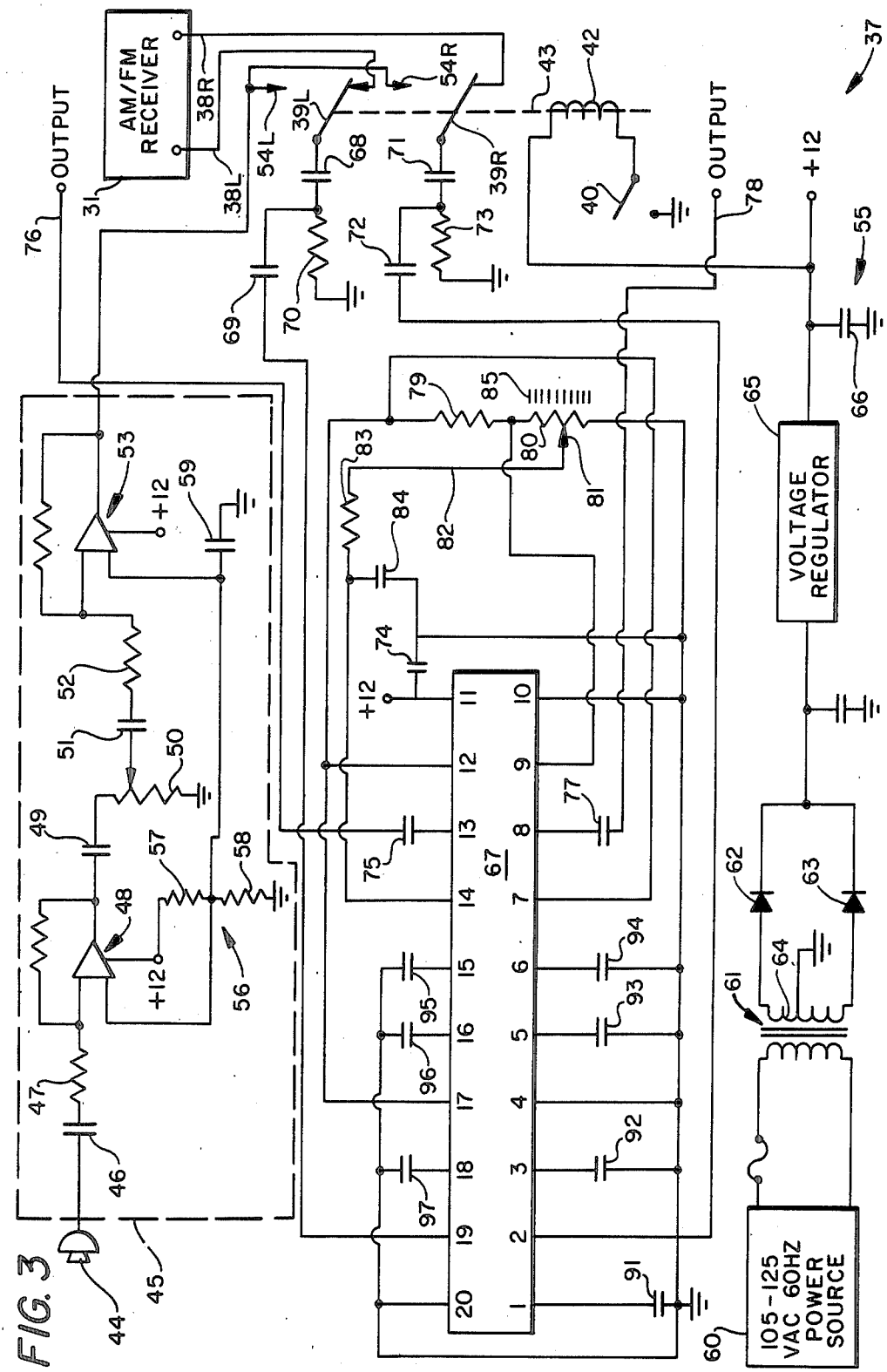
Figure 8:
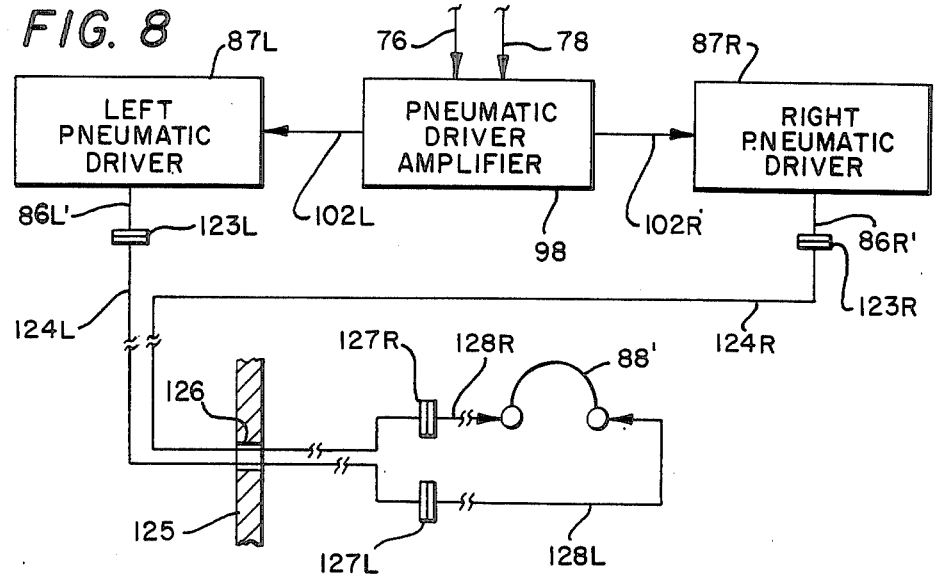
Figure 9:
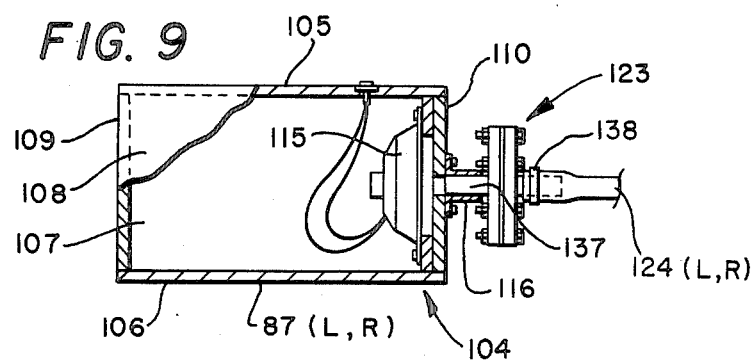
Figure 10:
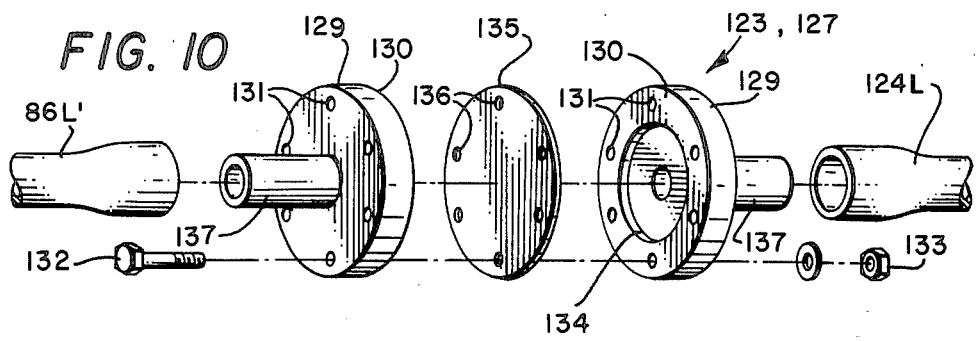

In the drawings:

FIG. 1 represents a block schematic diagram of a frequency attenuation compensated pneumatic headphone and tube audio system for medical scan room patient use;

FIG. 2, a combination schematic and block diagram after the AM/FM receiver (or other program source) through to the pneumatic outputs;

FIG. 3, a shematic diagram showing detail of the microphone amplifier and the compensation amplifier;

FIG. 4, a perspective view of one of the pneumatic driver speaker boxes;

FIG. 5, a side elevation of the pneumatic driver speaker box with a pneumatic tube fastened in place to the output opening of the box;

FIG. 6, a front elevation view of a front cavity bulkhead mounting the loudspeaker within the pneumatic driver speaker box;

FIG. 7, a front elevation view of the front box end enclosure with an acoustic pneumatic tube opening for insertion connection of a pneumatic tube end;

FIG. 8, a partial block schematic with the portion removed the same as the showing of that portion of FIG. 1 and with the left and right pneumatic drivers each serially connected, respectively, through a short section of pneumatic tubing, a pneumatic to liquid line acoustic transducer, an extended length of closed liquid acoustic line, a liquid line to pneumatic line acoustic transducer, a relatively short length of pneumatic tubing to a pneumatic head phone for medical scan room patient use;

FIG. 9, a partially broken away and sectioned side elevation view of a pneumatic driver speaker box directly connected to a pneumatic to liquid line transducer; and FIG. 10, an exploded perspective view of a pneumatic to liquid line acoustic transducer such as used in the acoustic system embodiments of FIGS. 8 and 9.

Referring to the drawings:

The frequency attenuation compensated pneumatic headphones and tube audio system 30 of FIG. 1 for medical scan room use is equipped with a standard off the shelf AM/FM stero receiver 31, such as a Pioneer SX40 receiver, equipped for receiving stereo inputs from a standard cassette tape deck 32, such as a Pioneer CT-50R, and providing stereo output to left monitor speaker 33 and right monitor speaker 34 when switch and volume control 35 is switched for monitor. When switch 36 is turned on stereo programming is fed to the stero compensation amplifier 37 (referring also to FIG. 2) through left stereo line 38L and right stereo line 38R and relay switches 39L and 39R when foot switch 40 is in the open state shown to the stereo compensation amplifier 37 in the compensation amplifier and microphone amplifier section 31. However, when foot switch 40 is depressed to the closed state electric DC power is applied through relay coil 42 that acting on its relay armature and rod 43 switches the relay switches 39L and 39R to close the circuits for operators microphone 44 activation input through microphone 44 amplifier circuit 45, in circuit section 41, to the stereo compensation amplifier 37 and simultaneous disconnect of the stereo input thereto from AM/FM stereo receiver 31.

Referring also to FIG. 3 the microphone amplifier circuit 45 includes connection from microphone 44 through capacitor 46 and resistor 47 to the first amplifier stage 48 having an output connection through capacitor 49, volume adjustment potentiometer 50, capacitor 51 and resistor 52 to second amplifier stage 53 that has an output connection to the normally open contacts 54L and 54R of relay switches 39L and 39R. DC voltage is applied from the power supply 55 directly to the first and second amplifier stages 48 and 53, respectively, and also via a voltage divider 56, with resistors 57 and 58 and connection through capacitor 59 to ground, as an additional voltage reference input to the first and second amplifier stages.

The power supply 55 includes connection from a 105–125 volt AC 60 Hz source 60 through transformer 61 with rectifier diodes 62 and 63 connected to opposite ends of center grounded transformer secondary coil 64 developing a DC output applied through voltage regulator 65. There is a 0.22 $\mu f$ capacitor 66 connection to ground on the DC output of the voltage regulator 65 connected as a DC voltage power supply to the microphone amplifier 45 and to the stereo compensation amplifier 37.

The stereo compensation amplifier 37 includes an integrated circuit chip 67 (that may be a National Semiconductor Co. chip LM-1035) that is a twenty terminal chip 67. Switch 39L is connected through capacitors 68 and 69, having a common junction connection through resistor 70 to ground, to terminal 19 of chip 67 as the left stereo input, and switch 39R is connected through capacitors 71 and 72, having a common junction connection through resistor 73 to ground, to terminal 2 of chip 67 as the right stereo input to the stereo compensation amplifier 37. The DC voltage supply out of voltage regulator 65 is connected to terminal 11 of chip 67 and also through capacitor 74 to ground and terminals 4, 10 and 20 of chip 67 are connected directly to ground. Terminal 13 of chip 67 is connected through capacitor 75 and line 76 as the left stereo output, and terminal 8 is connected through capacitor 77 and line 78 as the right stereo output from the stereo compensation amplifier 37. Terminals 7, 12 and 17 of chip 67 are connected serially through resistor 79 and the total resistance of potentiometer 80 to ground with the junction of resistor 79 and potentiometer 80 connected to terminal 9. The adjustably moveable tap 81 of potentiometer 80 is connected through line 82 and resistor 83 to terminal 14 of chip 67, with terminal 14 also connected through capacitor 84 to ground, and is set to graduated settings 85 as driven by setting of knob 86 to the desired setting of knob graduations 87 corresponding to graduated settings 85. This adjusts for a particular length of plastic material pneumatic tubes 88L and 88R used in extending from left pneumatic driver 89L and right pneumatic driver 89R to plastic pneumatic headphone set 90. Chip 67 terminals are connected 1 through capacitor 91, 3 through capacitor 92, 5 through capacitor 93, 6 through capacitor 94, 15 through capacitor 95, 16 through capacitor 96, and 18 through capacitor 97 to ground.

The left stereo output 76 and the right stereo output 78 of stereo compensation amplifier 37 are connected as inputs to the pneumatic driver amplifier circuit section 98 and extend to stereo control amplifier 99 that has a left stereo output line 100L connection to left stereo pneumatic driver amplifier 101L, and to amplifier 99 having a right stereo output line 100R connection to right stereo pneumatic driver amplifier 101R. The output lines 102L and 102R of left and right pneumatic driver amplifiers 101L and 101R, respectively, are connected as inputs to pneumatic tube drivers 87L and 87R, respectively. The DC power output of power supply 55 is extended through branches of DC line system 103 as power inputs to stereo control amplifier 99, and pneumatic driver amplifiers 101L and 101R in addition to the stereo compensation amplifier 37, microphone amplifier 45 and relay coil 42. In this system the potentiometer 80 is calibrated in pneumatic tubing (86L and 86R) lengths so that the installer measures the tubing length and then adjusts the potentiometer tap 81 accordingly. The compensation amplifier 37 has left and right RC networks including capacitor 68 and resistor 70, and capacitor 71 and resistor 73, respectively, that set the low frequency roll-off such that the headphone response is essentially flat with approximately ten foot left and right lengths of pneumatic tubing. Compensation is then attained with the compensation amplifier 37 providing varying amounts of low frequency roll-off compensation pneumatic tube length variation in left and right channels from ten to forty feet and more if needed. This frequency attenuation compensated pneumatic headphone and tube audio system for medical use makes use of a commercially available amplifier for the pneumatic driver amplifiers. Component sections of the system manufactured especially for the system include the compensation and microphone amplifier section and the pneumatic tube drivers. The system is to be supplied with a standard AM/FM receiver, cassette tape player (or recorder/player) along with the compensation amplifier, the pneumatic driver amplifier system, two pneumatic tube drivers, two monitor speakers, microphone, footswitch, pneumatic tubing, plastic headphones, installation hardware and wire connecting pneumatic driver amplifiers, and with pneumatic tubing in matched lengths.

Referring also to FIGS. 4 through 7 for pneumatic driver speaker box detail each pneumatic tube driver 87 (L, R) is shown to be a rectangular box 104 with top 105, bottom 106 opposite sides 107 and 108, a back 109 and a front end 110 with acoustic pneumatic tube opening 111. A bulk-head 112 provided with a cylindrical cavity 113 is mounted in the box 104 to the inside back of front end 110 as by screws through openings 114. A high compliance four inch diameter, permanent magnet loudspeaker 115 is mounted on the back of the bulkhead 112 in a conventional manner with the loudspeaker 115 aligned with and substantially the diameter of the cone and with a depth of approximately three quarters of an inch. The cavity behind the loudspeaker 115 has a cross sectional area of thirty six square inches (6" by 6") and a depth of approximately six and three quarter inches with a volume of approximately two hundred forty cubic inches. This configuration presented a pneumatic driver that is relatively efficient, with no serious response variations, that functions with virtually any high quality amplifier without requiring any other compensation. A plastic tube 86 (L, R) is mounted with the end thereof in opening 111 by a fitting 116 mounted on the front of front end 110 by screws 117 extended into openings 118. Power lines 119 and 120 for speaker 115 extend from connection terminals 121 and 122 on top 105 of box 104 down within the rear cavity within box 104 to speaker 115.

In a working embodiment of the compensation amplifier 37 typical values of some of the component values are for capacitors 68, 69, 71, 72, 75, 77, 84, 92 and 97—0.22 $\mu f$, capacitor 74 0.01 $\mu f$, resistor 79—20K ohms, potentiometer 80—20K ohms, resistor 83—47K ohms, capacitor 91—47 $\mu f$, capacitors 93 and 96—10 $\mu f$ and capacitors 94 and 95—0.1 f. These component values work well with chip 67 in providing the frequency amplification compensation desired along with settings of potentiometer tap 81 for different lengths of tubing 86L and 86R from 10 feet to 50 feet or more by, generally, ten foot settings. Thus, a compensation amplifier is provided with a wide range of frequency compensations to adjust response for varying lengths of pneumatic tubes particularly with the pronounced high frequency attenuation that occurs as sound travels through pneumatic tubes. As pneumatic tubes are made longer, more high frequency attenuation occurs, so that with more tube length more compensation is required. When monitor speakers 33 and 34 are switched on they present the programming without compensation so that the operator can listen to the programming being provided for the patient in its normal state comparable to the way the patient hears the programming out of the headset. The microphone amplifier 45 is provided to amplify the microphone signal to approximate amplitude of the program information signaling from the AM/FM receiver 31 to the compensation amplifier 37. This allows the operator to speak to the patient with little or no noticeable change in volume from the program signalling or information. This is with the microphone amplifier connected to the input of the compensation amplifier for frequency shaping when the microphone is used for operator to patient communication.

With the left and right inputs to the compensation amplifier duplicate RC networks set the low frequency roll off such that the headphone response is essentially flat with approximately ten feet of pneumatic tubing. The compensation then is able to provide varying amounts of low frequency roll off to compensate increasing pneumatic tube lengths in the range of ten to forty feet and more. The potentiometer 80 is roughly calibrated in pneumatic tubing lengths so that the installer measures the tubing length and then adjusts the potentiometer tap 81 accordingly.

Magnetic resonance scan rooms are shielded enclosures (radio frequency and sometimes magnetic shielded) with dimensions typically of approximately twenty by thirty feet with a height of approximately twelve feet. Visually the room employs a "dropped" ceiling suspended by an aluminum grid that is hung from non-magnetic stainless steel wires. An entrance door is provided in the end of the room for viewing the patient. The patient communication and music system employs a pneumatic headset of the type used for aircraft passenger entertainment with the headset connected however to pneumatic tubes attached to the patient bed (liquid filled tubes may not be used within the "bore" of the scan magnet because most practical liquids include compounds of hydrogen that are not transparent to the scan field).

Referring also to FIGS. 8, 9 and 10 the left and right pneumatic drivers 87L and 87R are connected serially, respectively, through pneumatic to liquid line acoustic transducers 123L and 123R to liquid lines 124L and 124R that extend through room wall 125 opening 126 to liquid line to pneumatic acoustic transducers 127L and 127R connected to pneumatic lines 128L and 128R on through to plastic non-magnetic and magnetic field transparent pneumatic headphone set 88'. The transducers 123 and 127 are all alike with opposite ends 129 being duplicates of each other having a rim 130 with bolt holes 131 spaced around the rim so that bolt 132 and nut 133 assemblies may bolt the transducer together. Each end 129 is formed with an internal recess 134 to accomodate acoustic vibrations of the diaphragm 135 with bolt holes 136 between ends 129 in the transducer assembly and a tube extension 137 extends outward from each end 129 for connection of the transducer in the acoustic circuits with a clamp 138, such as shown in FIG. 9, used to clamp pneumatic line 86L' on a tube extension 137 and an additional clamp 138 to clamp liquid line 124L on a tube extension 137.

The pneumatic tubes (which are attached to the patient bed or close to the bed) are connected to either pneumatic or hydraulic (liquid filled) tubes which run to the wall of the scan room or penetrate the wall of the scan room. In the case of pneumatic tubes, they penetrate the scan room wall through wave guides. Hydraulic tubes may either penetrate the scan room wall (through waveguides) or they may connect to pneumatic tubes which penetrate the scan room wall (through waveguides). The option is provided in cases where the available space through the wall openings or waveguides is not great enough to allow the ends of the hydraulic tubes to pass (the ends being larger than the tubes).

Typical tube set lengths are:
1. From the pneumatic drivers 87 (L and R) to the scan room wall six feet or less.
2. From the scan room wall to the patient bed fifteen to thirty feet.
3. From connection to the patient bed to the patient headphones ten to fifteen feet.

Overall tube system set lengths generally are in the range from twenty feet to fifty feet. Hydraulic (liquid) tube lines would be provided in standard lengths of approximately thirty feet (filled and sealed at the factory). When liquid tube lines are used the total pneumatic tube length by sets should be held to less than fifteen feet to minimize higher frequency loss power compensation requirements. Liquid (or hydraulic) tubes are used to replace a major portion of the pneumatic tubes otherwise used in this acoustic system. These hydraulic tubes are filled with an incompressible fluid which yields a faster propagation rate down the tubes with greatly reduced power loss and improved high-frequency response as compared to pneumatic tubes. While the high-frequency losses are rather insignificant with pneumatic tube lengths of five feet or less, these losses are quite significant with tube lengths of more than thirty feet. The original application, using pneumatic tubes, employed a large amount of compensation to counteract these losses. While compensation is still provided with the hydraulic system, the amount of this compensation has been greatly reduced.

Advantage of using the hydraulic tubes include:
A. Improved frequency response (improved fidelity).
B. Reduced power required to produce the same sound pressure level at the headphones.

Description of hydraulic tubes:

The tube material is plastic of a semi-rigid type (nylon or polyethylene) with a diameter of ¼ or ⅜ inches (tubes may be made larger or smaller). Attached to each end of this tubing 124 is a fitting containing a flexible diaphragm 135 which moves in response to air or fluid pressure exerted upon it. This diaphragm 135 is used to to "seal" the ends of the tube 124 containing the fluid, and provides on air to fluid interface coupling. In use, the driver transducer 104 exerts air pressure upon the diaphragm 135 which in turn attempts to compress the fluid within the tubes 124. Since the fluid is virtually incompressible, the diaphragm 135 at the other end of the tube 124 responds in like manner to the diaphragm 135 at the driven end. Because the fluid medium is incompressible, there is virtually no loss due to compressibility of the medium, and in fact the losses due to compressibility are attributible to the fact that the walls of the tubes are not totally rigid (these losses are rather small even for tube lengths in excess of fifty feet and contribute only slightly larger losses when the medium is a liquid instead of gas (air).

The diaphragms 135 at either end of the hydraulic tubes 124 may be made any practical size or shape, but the prototype tube was constructed with a diaphragm diameter of approximately one inch. The prototype diaphragm was circular in shape for convenience of construction and because this form factor allows a uniform driving surface (no corners to contend with). The prototype diaphragm was constructed of mylar but it could be constructed of any other flexible material which is compatible with the fluid used. The holding fixture was constructed with a cavity on either side of the diaphragm to allow free movement of the diaphragm. For convenience, the hydraulic tube ends could be made smaller than one inch in diameter so that they could be passed through one inch waveguides for penetration into the shielded scan room. Larger hydraulic tube ends could easily be used by employing a short length of pneumatic tubing between the hydraulic tube ends and the driving transducer.

Pneumatic headphones are used at the receiving ends of the hydraulic tubes (either directly connected to the diaphragm fittings or through a short piece of pneumatic tubing connected between the hydraulic tube and the headphone tubes).

The prototype hydraulic tube was filled with water, but production models would most likely be filled with some other liquid (mineral oil, fluorcarbon compounds, etc. ). The prototype was gravity filled by closing one end of the tube and holding the tube vertically. After the tube was filled, the second diaphragm was installed so that the tube was completely filled with liquid. Several better methods of filling the tube on a production basis are being considered, including the use of a fill valve located on the tube.

In summary, the liquid tubes would replace the major portion of the pneumatic tubes presently used. There would be pneumatic to liquid interface at either end of the liquid tubes (although these might be as short as an inch or so on the driving end, and as short as two or three feet on the receiving end).

With the embodiment of FIG. 9 the pneumatic driver speaker box 104 is directly connected to a pneumatic to liquid line 124 acoustic transducer 123 with pneumatic lines 128 L and 128R connected to headset 88' at the patient bed being the only pneumatic lines of the system.

Whereas this invention has been described with respect to several embodiments thereof, it should be realized that various changes may be made without departure from the essential contributions to the art made by the teachings hereof.

I claim:

1. A frequency attenuation compensated pneumatic headphone and acoustic tube audio system comprising: pneumatic tube driver means; acoustic plastic tube means transparent to scanning fields such as a Nuclear Magnetic Resonance field and in a length range of approximately ten to fifty feet; plastic material pneumatic headphones for a user that are transparent to scanning signals so as to not cause interference with scanning signals; pneumatic tube driver means for driving audio signals through said acoustic plastic tube means and said pneumatic headphones to the ears of a user; program signal source means; a frequency response compensation amplifier connected to the output of said program signal source means that with progressively higher frequencies boosts the higher frequencies to compensate for the increasing attenuation of progressively higher frequencies as audio is passed through said acoustic tube means; circuit means interconnecting said compensation amplifier and said pneumatic tube driver means; including pneumatic driver amplifier means interconnecting said compensation amplifier and said pneumatic tube driver means; wherein said program signal source means is a stereo signal source; said compensation amplifier is a stereo signal two channel amplifier; monitor speaker means is connected directly to said program signal source means; said pneumatic driver amplifier means includes a stereo control amplifier and left and right pneumatic driver amplifiers; and wherein said compensation amplifier includes settable resistance valve means for adjusting higher frequency boost compensation for different length acoustic plastic tube means of substantially matched pair lengths used in different installations.

2. The frequency attenuation compensation pneumatic headphone and tube audio system of claim 1, wherein a microphone and microphone amplifier are included with the audio system also including switch means in the input circuit path to said compensation amplifier connected to the output of said microphone amplifier and connected to the output of said program signal source means and controllable for switching between said program signal source means and said microphone amplifier.

3. The frequency attenuation compensation pneumatic headphone and tube audio system of claim 2, wherein said switch means is a relay switch connected to an operator operated power switch.

4. The frequency attenuation compensation pneumatic headphone and tube audio system of claim 1, wherein said settable resistance value means is a potentiometer with an adjustably settable tap.

5. The frequency attenuation compensation pneumatic headphone and tube audio system of claim 1, wherein pneumatic plastic tube means is included in said acoustic plastic tube means; and said compensation amplifier has RC input network means that sets low frequency roll-off such that headphone response is essentially flat with shorter lengths of pneumatic tubing in the ten foot to twenty foot range.

6. The frequency attenuation compensated pneumatic headphone and tube audio system of claim 1, wherein pneumatic plastic tube means is included in said acoustic plastic tube means; and said pneumatic driver means includes a box means enclosing a loudspeaker means with cavity means between the loudspeaker and the front end wall of the box; a hole in said end wall in open communication with said cavity means; and with a tubing end of said pneumatic plastic tube means received in said hole in said end wall for importing into and through the tubing audio signalling generated in said loudspeaker.

7. The frequency attenuation compensated pneumatic headphone and tube audio system of claim 6, wherein said box means comprises two used as said pneumatic driver means one a left pneumatic driver and the other a right pneumatic driver connected to left and right pneumatic plastic tubes of approximately the same length that in turn are extended to and feed left and right stereo signals to left and right earphones, respectively, of said plastic material pneumatic headphones.

8. The frequency attenuation compensated pneumatic headphone and tube audio system of claim 1, wherein said program signal source is a left and right channel stereo program signal source; said compensation amplifier is a two channel stereo amplifier; and said pneumatic tube driver means is a two speaker boxes each enclosing a loud speaker and feeding audio signals to a pneumatic plastic tube portion of said acoustic plastic tube means connected to each; and with the two tubes of approximately the same length connected to left and right earphones of a headset.

9. The frequency attenuation compensated pneumatic headphone and tube audio system of claim 8, wherein said circuit means includes pneumatic driver stereo amplifier means interconnecting said two channel stereo amplifier and said two speaker boxes comprising said pneumatic driver means.

10. The frequency attenuation compensated pneumatic headphone and tube audio system of claim 9, wherein said compensation amplifier has an RC input network means in each of two input channels that set low frequency roll-off such that headphone response is essentially flat through shorter lengths of said pneumatic tube portion in the ten foot to twenty foot range.

11. The frequency attenuation compensated pneumatic headphone and tube audio system of claim 10, wherein each of said boxes encloses a loudspeaker on a cavity wall with a cavity between the loudspeaker and a front wall of the box; a hole in said front wall in open communication with said cavity; a resonant chamber behind the loudspeaker; and with a tubing end of said pneumatic plastic tube portion received in said hole in said front wall for imparting into and through the tubing audio signalling generated in said loudspeaker.

12. The frequency attenuation compensated pneumatic headphone and tube audio system of claim 11, wherein a microphone and microphone amplifier is included with the audio system; switch means is included in the left and right channel input circuits paths to said stereo compensation amplifier; and with said switch means connected to the output of said microphone amplifier and connected to the left and right channel outputs of said stereo program signal source means; and wherein said switch means is a multi-contact relay switch connected to an operator controlled power on/off switch.

13. The frequency attenuation compensated pneumatic headphone and tube audio system of claim 1, wherein said acoustic tubing includes both pneumatic plastic tubing and liquid plastic tubing.

14. The frequency attenuation compensated pneumatic headphone and tube audio system of claim 13, wherein the pneumatic plastic tubing is included in a left channel and in a right channel of said acoustic tubing.

15. The frequency attenuation compensated pneumatic headphone and tube audio system of claim 14, wherein the total length of pneumatic plastic tubing is substantially equal between said left and right channels of acoustic tubing.

16. The frequency attenuation compensated pneumatic headphone and tube audio system of claim 15, wherein most of the acoustic tubing length in both said left and right channels is liquid plastic tubing.

17. The frequency attenuation compensated pneumatic headphone and tube audio system of claim 16, wherein said liquid plastic tubing is made up in sections with a liquid retaining diaphragm in a pneumatic to liquid acoustic transducer at each end of each of said liquid plastic tubing sections.

18. The frequency attenuation compensated pneumatic headphone and tube audio system of claim 17, wherein pneumatic tube lengths interconnect said pneumatic tube driver means and liquid plastic tubing sections in both said left and right channels; and pneumatic tube headphone section lengths interconnect said liquid plastic tubing sections and said pneumatic headphones.

19. The frequency attenuation compensated pneumatic headphone and tube audio system of claim 17, wherein a pneumatic to liquid acoustic transducer of each of said liquid plastic tubing sections is directly connected to said pneumatic tube driver means.

* * * * *